(12) United States Patent
Chen et al.

(10) Patent No.: US 10,731,024 B2
(45) Date of Patent: Aug. 4, 2020

(54) SUPERABSORBENT POLYMER AND THE METHOD OF FABRICATING THE SAME

(71) Applicant: Formosa Plastics Corporation, Kaohsiung (TW)

(72) Inventors: Zhong-Yi Chen, Pingtung County (TW); Yu-Yen Chuang, Kaohsiung (TW); Li-Han Huang, Kaohsiung (TW); Yu-Sam Lin, Kaohsiung (TW); Feng-Yi Chen, Pingtung County (TW); Ching-Hua Liang, New Taipei (TW)

(73) Assignee: FORMOSA PLASTICS CORPORATION, Kaohsiung (TW)

( * ) Notice: Subject to any disclaimer, the term of this patent is extended or adjusted under 35 U.S.C. 154(b) by 162 days.

(21) Appl. No.: 15/831,349

(22) Filed: Dec. 4, 2017

(65) Prior Publication Data

US 2018/0282507 A1 Oct. 4, 2018

(30) Foreign Application Priority Data

Mar. 31, 2017 (TW) .............................. 106111089 A (51) Int. Cl.
  *C08F 20/06* (2006.01)
  *C08K 3/34* (2006.01)
  (Continued)

(52) U.S. Cl.
  CPC ................ *C08K 3/36* (2013.01); *A61L 15/18* (2013.01); *A61L 15/46* (2013.01); *A61L 15/60* (2013.01); *B01J 20/08* (2013.01); *B01J 20/10* (2013.01); *B01J 20/267* (2013.01); *C08J 3/128* (2013.01); *C08J 3/215* (2013.01); *C08J 3/24* (2013.01); *C08J 3/245* (2013.01); *C08K 3/22* (2013.01); *C08K 3/346* (2013.01); *C08L 33/02* (2013.01); *C08L 57/06* (2013.01); *C08L 101/14* (2013.01); *A61L 15/24* (2013.01); *B01J 20/16* (2013.01);
  (Continued)

(58) Field of Classification Search
  None
  See application file for complete search history.

(56) References Cited

U.S. PATENT DOCUMENTS

| 6,124,391 A * | 9/2000 | Sun .......................... A61L 15/18 523/223 |
| 2014/0031473 A1 * | 1/2014 | Nogi ....................... C08F 20/06 524/320 |
| 2016/0074550 A1 * | 3/2016 | Loick ................. B01J 20/28016 424/405 |

FOREIGN PATENT DOCUMENTS

| CN | 101045789 A | 10/2007 |
| CN | 101333260 A | 12/2008 |

(Continued)

OTHER PUBLICATIONS

Show Denko, Product Guide for High Silica Zeolite. Retrieved on Jul. 10, 2019. (Year: 2019).*

*Primary Examiner* — Richard A Huhn
(74) *Attorney, Agent, or Firm* — Muncy, Geissler, Olds & Lowe, P.C.

(57) ABSTRACT

A superabsorbent polymer includes polymer particles, surface cross-linking agents and particles made of silicon-containing inorganic salt. The polymer particles have cross-linking inside the polymer particles. The surface cross-linking agents are covalently bound to the surface of the polymer particles so as to constitute a surface cross-linked region at the surface of each said resin particle, and the particles made of silicon-containing inorganic salt cover the surface of the polymer particles.

5 Claims, 2 Drawing Sheets

(51) Int. Cl.

| | | |
|---|---|---|
| *A61L 15/18* | (2006.01) | |
| *B01J 20/16* | (2006.01) | |
| *C08J 3/12* | (2006.01) | |
| *C08K 3/36* | (2006.01) | |
| *B01J 20/10* | (2006.01) | |
| *B01J 20/08* | (2006.01) | |
| *A61L 15/46* | (2006.01) | |
| *A61L 15/60* | (2006.01) | |
| *C08K 3/22* | (2006.01) | |
| *C08L 101/14* | (2006.01) | |
| *C08J 3/215* | (2006.01) | |
| *C08L 33/02* | (2006.01) | |
| *B01J 20/26* | (2006.01) | |
| *C08J 3/24* | (2006.01) | |
| *C08L 57/06* | (2006.01) | |
| *C09D 7/62* | (2018.01) | |
| *A61L 15/24* | (2006.01) | |
| *C08L 33/04* | (2006.01) | |

(52) U.S. Cl.
CPC .......... *B01J 20/165* (2013.01); *B01J 2220/68* (2013.01); *C08F 20/06* (2013.01); *C08J 3/12* (2013.01); *C08J 2300/14* (2013.01); *C08J 2333/02* (2013.01); *C08K 3/34* (2013.01); *C08K 2003/2227* (2013.01); *C08L 33/04* (2013.01); *C09D 7/62* (2018.01)

(56) References Cited

FOREIGN PATENT DOCUMENTS

| CN | 104788871 A | 7/2015 |
|---|---|---|
| WO | 00/10619 | 3/2000 |
| WO | 2015/163522 A1 | 10/2015 |

\* cited by examiner

SUPERABSORBENT POLYMER AND THE METHOD OF FABRICATING THE SAME

BACKGROUND OF THE INVENTION

1. Field of the Invention

The present invention relates to a water-absorbent resin and a method for producing the same. In particular, the present invention is directed to a water-absorbent resin with a resin surface which is modified with an inorganic substance and a method for producing the same.

2. Description of the Prior Art

Water-absorbent resin is widely used in agricultural or horticultural aspects as water-retaining agents, anti-dew condensation agents in building materials, and materials for removing moisture from petroleum, or outer water-proof coatings on cables and hygiene supplies such as diapers, women's hygiene products, and disposable wipes etc., especially mostly used in the diapers.

The current main direction for development is functional diapers, in particular adult diapers. In addition to emphasizing the absorption capacity and dryness, bacteriostatic and deodorant abilities are further directed to. Based on this demand, a variety of researches are carried out to develop the absorbent resin of bacteriostatic and deodorant abilities and capable of maintaining the water absorption feature.

The conventional method of antibacterial or deodorizing ability is to use zeolite particles to be dispersed inside the absorbent resin to equip the absorbent polymer with a deodorizing ability (U.S. Pat. No. 5,980,879), which discloses the addition of zeolite particles in a polymeric reaction to make the absorbent resin have a deodorizing ability, but the absorption capacity of the water absorbent resin is greatly reduced due to the addition amount of the zeolite at least about 25%. U.S. Patent Application No. 20150290052 uses activated carbon or zeolite particles to be added to the diaper absorbent to similarly have the deodorizing ability, but the particles leak in the production equipment, and even suspend in the plant air to cause a certain degree of damages to the on-site personnel' health.

WO 2009/048145 discloses a method for preparing an absorbent resin by adding a bamboo extract or a tea extract onto the surface of an absorbent resin or to a polymeric reaction. However, since the extracts affect the polymeric reaction, not only it reduces the water absorption capacity of the absorbent resin, but also makes more residual monomers left in the absorbent resin so that swelling is caused by the contact with the skin. In addition, U.S. Patent Publication No. 20030004479 and U.S. Patent Publication No. 20040048955 propose that the powder obtained from pulverized bamboo or tea is added to the surface of the absorbent resin but the resultant antibacterial and deodorant ability is poor because the dispersibility of the powder of the pulverized bamboo or tea is low and the mixture with the absorbent resin is uneven.

In addition, the use of activated carbon or nano-silver ions or zeolite surface coated with silver ions is also possible to reduce the occurrence of odor or bacterial growth (U.S. Pat. No. 6,663,949, European Patent No. EP1404385 and U.S. Pat. No. 7,868,075). European Patent EP 1275404 discloses the use of cyclodextrin or its derivatives to be mixed with absorbent resin to reduce the occurrence of odors. In addition, U.S. Patent Publication No. 20150306272 discloses the thermal treatment of 1,2-decanediol and absorbent resin to reduce the occurrence of odor. However, the above methods cannot have both antibacterial and deodorant abilities, and only have a better ability to inhibit ammonia.

WO 2003/028778 discloses that the pH of the absorbent resin is lowered to prepare an antibacterial absorbent resin. U.S. Patent Publication No. 20010053807 discloses that the addition of aminoacetic acid reduces the occurrence of odor, but the absorbent resin obtained by the above methods has bad urine tolerance under pressure.

Japanese Patent Publication No. 1995-165981 discloses a mixture having a water-absorbent resin and a phosphate compound. Japanese Patent Application No. 1999-116829 discloses mix of absorbent resin and a silicate compound to improve the bacteriostatic ability of the water-absorbent resin, but it will reduce the absorption against pressure (AAP, tested under ERT 442.3(10) of EDANA).

U.S. Pat. No. 8,658,146 discloses the use of Gallotannin and its derivative to be mixed with a water-absorbent resin. Although it is able to obtain a water-absorbent resin having a deodorizing ability, its cost is high and it is not suitable for long-term preservation due to a yellow or brown problem under high temperature and high humidity.

In view of these, it is still necessary to provide a water-absorbent resin which has both antibacterial and deodorizing abilities and does not reduce the water absorption characteristics to solve the drawbacks of the current water-absorbent resin.

SUMMARY OF THE INVENTION

According to one embodiment of the present invention, a superabsorbent polymer is provided. The superabsorbent polymer includes resin particles, a surface-crosslinking agent, and silicon-containing inorganic salt-containing particles. Each resin particle has an internal crosslinking structure. The surface-crosslinking agent is bonded to a surface of each resin particle so as to constitute a surface cross-linked region at the surface of each resin particle. The silicon-containing inorganic salt-containing particles cover the surface of each the resin particle.

According to another embodiment of the present invention, a method for producing a superabsorbent polymer is provided. First, an acid-based monomer aqueous solution is provided and a radical polymerization reaction is carried out to obtain a superabsorbent polymer having an internal crosslinking structure. Second, the superabsorbent polymer is cut to obtain multiple superabsorbent polymer particles. Then, a surface-crosslinking agent is added to a surface of each superabsorbent polymer particle and a heat treatment is carried out. Afterwards, an aqueous solution having silicon-containing inorganic salt-containing particle is applied to the surface of each superabsorbent polymer particle.

In another embodiment of the present invention, each resin particle is made from polymerized hydrophilic monomers having an unsaturated double bond.

In another embodiment of the present invention, each silicon-containing inorganic salt-containing particle includes alumina and silicon oxide.

In another embodiment of the present invention, alumina and silicon oxide in the silicon-containing inorganic salt-containing particles have a weight ratio between 0.7 and 0.95.

In another embodiment of the present invention, each silicon-containing inorganic salt-containing particle has a particle size between 1 and 10 μm.

In another embodiment of the present invention, each silicon-containing inorganic salt-containing particle is composed of kaolinite.

In another embodiment of the present invention, the pH value of the aqueous solution is between 4 and 6.5.

In another embodiment of the present invention, the superabsorbent polymer particles in the aqueous solution have a weight percentage of 0.5% to 20%.

The superabsorbent polymer resin provided by the examples of the present invention has both antibacterial and deodorizing abilities and still has a certain degree of water absorption property. Further, the superabsorbent polymer resin produced by the examples of the present invention has excellent absorption characteristics to synthetic urine, and excellent antibacterial and deodorizing functions, and does not cause the particles to leak in the production equipment and does not even suspense in the air of a plant, so it can effectively reduce the risk of the damages to the on-site personnel' health.

These and other objectives of the present invention will no doubt become obvious to those of ordinary skill in the art after reading the following detailed description of the preferred embodiment that is illustrated in the various figures and drawings.

DETAILED DESCRIPTION

In the following paragraphs, embodiments of a superabsorbent polymer, a.k.a. an absorbent resin or a water-absorbent resin, and a method for producing the superabsorbent polymer are given so that those of ordinary skills in the art are able to practice the present invention. These embodiments are accompanied by the corresponding drawings so that the drawings constitute a part of the embodiments. While the embodiments of the invention are disclosed as follows, it is not intended to limit the scope of the invention, and any parson skilled in the art may modify it without departing from the spirit and scope of the invention.

According to one embodiment of the present invention, a method for producing a superabsorbent polymer is provided in order to produce a superabsorbent polymer having both antibacterial and deodorizing abilities without reducing the water absorption characteristics. Hereinafter, the method for producing the superabsorbent polymer according to embodiments of the present invention will be described.

According to one embodiment of the present invention, a method for producing a superabsorbent polymer is provided. The method includes at least the following steps. A water-soluble unsaturated monomer aqueous solution having a neutralization ratio of 45 mol % or more, such as an acid-based monomer aqueous solution, is provided. Thereafter, the acid-based monomer aqueous solution is subjected to a radical polymerization reaction with a polymerization initiator to form a hydrogel with a corresponding composition. Followed by cutting the hydrogel, small hydrogel pieces are obtained. Thereafter, the hydrogel pieces are dried, pulverized and screened at a temperature of 100° C. to 250° C. in order to obtain a superabsorbent polymer, also known as a water-absorbent resin or an absorbent resin. Next, a surface cross-linking reaction is carried out on the surface of the superabsorbent polymer. After the crosslinking reaction, a silicon-containing compound weak acid aqueous solution is further added to carry out a surface treatment on the surface of the superabsorbent polymer.

The above-mentioned water-soluble unsaturated monomer may be selected from a water-soluble monomer having an unsaturated double bond and an acidic group, such as acrylic acid, methacrylic acid, marinic acid, fumaric acid, 2-propenylamine-2-methylpropanesulfonic acid, maleic acid, maleic acid anhydride, fumaric acid, fumaric acid anhydride and the like. The selection of the monomer is not limited to one single monomer so various monomers may be combined together. In addition, other hydrophilic monomers having an unsaturated double bond may be optionally added, for example, acrylamide, methacrylamide, 2-carboxyethyl acrylate, 2-carboxyethyl methacrylate, methyl acrylate, ethyl acrylate, N-dimethyl acrylamide, and N-trimethyl acrylamide ammonium chloride, and it is suggested that the added amount does not deteriorate the physical properties of the superabsorbent polymer.

The above-mentioned water-soluble unsaturated monomer may be selected from water-soluble monomers having an unsaturated double bond having an acidic group such as acrylic acid, methacrylic acid, marinic acid, fumaric acid, 2-propenylamine-2-methylpropanesulfonic acid, maleic acid, maleic anhydride, fumaric acid, fumaric anhydride and the like. Monomer selection is not specific restrictions can only use one, can also be combined with a variety of monomers used together. In addition, it is also desirable to add other hydrophilic monomers having an unsaturated double bond, for example, acrylamide, methacrylamide, 2-carboxyethyl acrylate, 2-carboxyethyl methacrylate, methacrylic acid Ester, ethyl acrylate, dimethylamine propylene acrylamide, and chlorinated acrylated trimethylammonium chloride, but the amount is added so as not to impair the physical properties of the water absorbent resin.

The concentration of the monomer aqueous solution for the radical polymerization reaction is not limited. Preferably, the weight percentage of the monomer in the aqueous solution should be controlled between 20% and 55%, more preferably between 30% and 45%. When the weight percentage is less than 20%, the hydrogel is too soft and too sticky to be mechanically processed after the polymerization. However, when the monomer concentration is higher than 55% by weight, the monomer concentration is close to the saturated concentration so it is not easy to be formulated and the reaction is too fast to control the reaction heat. The pH value of the unsaturated monomer aqueous solution is preferably not less than 5.5. When the pH value is lower than 5.5, there are too many excessive monomer residues present in the hydrogel after the polymerization to result in poor physical properties of the resultant superabsorbent polymer.

Before the free radical polymerization reaction, a water-soluble polymer may be added to the monomer aqueous solution to reduce the cost. The above water-soluble polymer may be selected from: polymers such as partially saponified or fully saponified polyvinyl alcohol, polyethylene glycol, polyacrylic acid, polyacrylamide, starch, starch derivatives, methylcellulose, methylcellulose acrylate and ethyl cellulose. The molecular weight of the water-soluble polymer is not particularly limited, and the water-soluble polymer is preferably selected from starch, partially saponified or fully saponified polyvinyl alcohol or its mixture. The additive water-soluble polymer in the superabsorbent polymer has a weight percent between 0% and 20%, preferably between 0% and 10%, more preferably between 0% and 5%. When the amount of the added water-soluble polymer is more than 20%, the physical properties of the polymer is jeopardized so that the physical properties deteriorate.

A radical polymerization cross-linking agent may be added to the monomer solution prior to the radical polymerization reaction. By adding a radical polymerization cross-linking agent, the superabsorbent polymer after the reaction may be suitably cross-linked, to render the resultant superabsorbent polymer gel with appropriate processability. The radical polymerization cross-linking agent may be used singly or in combination of two or more. The weight percent of the radical polymerization cross-linking agent may be between 0.001% and 5%, based on the total solid content parts of the reactants, preferably between 0.01% and 3%. When the addition amount of the radical polymerization cross-linking agent is less than 0.001% by weight, the resultant hydrogel after the polymerization will be too soft and sticky to be advantageous in mechanical processing. When the addition amount of the radical polymerization cross-linking agent is 5% or more by weight, the water absorption property is too low, and the performance of the water absorbent polymer is lowered.

The above-mentioned radical polymerization cross-linking agent may be a compound having two or more unsaturated double bonds, for example, N,N'-bis(2-propenyl) amine, N,N'-methylene-bis(acrylamide), N,N'-methylene-bis(methacrylamide), allyl acrylate, ethylene glycol diacrylate, polyethylene glycol diacrylate, ethylene glycol dimethacrylate, poly ethylene glycol dimethacrylate, glycerol triacrylate, glycerol trimethacrylate, glycerol ethylene oxide triacrylate or trimethacrylate, trimethylolpropane ethylene oxide triacrylate or trimethacrylate, trimethylolpropane trimethacrylate, trimethylolpropane triacrylate, N,N,N-tris (2-propenyl)amine, ethylene glycol diacrylate, polyoxyethylene triacrylate glycerol esters, triethylene polyoxyethylene glycerol triacrylate, dipropylene triethylene glycol esters and the like, and compounds having two or more epoxy groups may be selected, for example, sorbitol polyglycidyl ether, polypropylene glycol Polyglycidyl ether, ethylene glycol diglycidyl ether, diethylene glycol diglycidyl alcohol Ether, polyethylene glycol diglycidyl ether, dipropylene glycol polyglycidyl ether and the like, but they are not limited to these.

In order to control the pH value of the finished product to make it neutral or slightly acidic, the carboxylic acid group of the acid-based monomer should be partially neutralized. The neutralizing agent for adjusting the pH may be a hydroxide or a carbonate compound of an alkali metal group or an alkaline earth metal group in the periodic table, such as sodium hydroxide, potassium hydroxide, sodium carbonate, potassium carbonate, sodium bicarbonate, potassium bicarbonate, ammonia compounds or their mixtures. The neutralizing agent may be used alone or in mixture. By adding a neutralizing agent, the carboxylic acid groups of the acid-based monomer are partially neutralized to form a sodium salt, a potassium salt or an ammonium salt. Preferably, the neutralizing mole concentration (the mole concentration of a neutralizing agent) is in the range of 45 mol % to 85 mol %, and more preferably 50 mol % to 75 mol %. When the neutralizing mole concentration is 45 mol % or less, the pH value of the finished products is too low, and when the neutralizing mole concentration is 85 mol % or more, the pH value of the finished products is too high. When the pH value of the finished products is not neutral or slightly acidic, it is not suitable for the direct contact with the human body, so it is less safe.

For the radical polymerization reaction described above, a polymerization initiator is usually added to the monomer solution. The radical polymerization reaction initiates with the generation of free radicals by the polymerization initiator. The appropriate amount of the polymerization initiator is between 0.001% and 10% by weight (based on the weight of the neutralized acrylate), preferably between 0.1% and 5% by weight. When the weight percentage is 0.001% or less, the reaction would be too slow to have economic benefits. When the weight percentage is 10% or more, the reaction is too fast so that the reaction heat is not easy to control and it tends to polymerize only too much to form a gel-like solid.

The above-mentioned polymerization initiator may be a thermal decomposition type initiator, a redox type initiator, or a mixture of both. For the thermal decomposition type initiator, it may be a peroxide or an azo compound. For example, the peroxide may be, for instance, hydrogen peroxide, di-t-butyl peroxide, a peroxyamide or a persulfate (ammonium salt, alkali metal salt), and the like. The azo compound may be, for example, 2,2'-azobis (2-amidinopropane) dihydrochloride salt, 2.2'-azobis (N,N-dimethyleneisobutylamidine) dihydrochloride salt. In addition, for the redox type initiator, it may be a reducing agent such as an acidic sulfite salt, a thiosulfate salt, ascorbic acid or a ferrous salt. Besides, the polymerization initiator may simultaneously include both a redox type initiator and a thermal decomposition type initiator. In the case of when the polymerization initiator includes both a redox type initiator and a thermal decomposition type initiator, the redox type initiator reacts at the initial stage of the radical polymerization reaction to produce radicals, and the polymerization reaction starts when the radicals are transferred to the monomer. Because temperature is raised by the enormous heat which is released during the polymerization reaction, the decomposition of the thermal decomposition type initiator proceeds when the temperature reaches the decomposition temperature of the thermal decomposition type initiator, which makes the entire polymerization reaction even more completed.

The above-described radical polymerization reaction may be carried out in a conventional batch reaction vessel or on a conveyor belt reactor. The bulk gel obtained from the reaction is then cut into small gel particles having a diameter of 20 mm or less using a crusher, and preferably less than 10 mm in diameter.

After the small gel particles are obtained, the subsequent screening step is carried out. In the screening step, it is preferable to collect gel particles having a diameter of 2.00 mm or less, more preferably between 0.05 mm and 1.50 mm. For gel particles having a particle size greater than 2.00 mm, they are sent back to the reactor for re-chopping. It is to be noted that it is easy to cause a higher amount of fine powder in the finished product if the gel particles having a particle diameter of 0.03 mm or less are dried and pulverized. When the gel particles having a diameter of 2.00 mm or more are dried, there are high residual monomers in the product and lead to shortcomings such as other poor physical properties due to poor heat conduction. According to one embodiment of the present invention, when the particle size distribution of the acrylate gel particles is narrower, not only the dried gel particles may have the best physical properties, but also the time and temperature of the drying can be advantageously controlled.

After the above screening step, the drying procedure is carried out. The drying temperature is preferably between 100° C. and 180° C. If the drying temperature is below 100° C., it leads to much longer drying time and to adverse economic benefits. If the drying temperature is above 180° C., the drying step will make the cross-linking agent prematurely undergo the cross-linking reaction and the residual monomer is unable to be removed efficiently in the subsequent process owning to an overly high cross-linking degree, which is unable to reduce the residual monomer.

After the above drying procedure, the pulverization and the screening of the fixed particle size are further carried out. The screening of the preferred fixed particle is between 0.06 mm and 1.00 mm, more preferably between 0.10 mm and 0.850 mm. When the particle size is below 0.06 mm, the fine particles will increase the dust of the finished product. When the particle size is more than 1.00 mm, the water absorption rate of the finished product becomes slow. According to an embodiment of the present invention, the particle size distribution of the acrylate polymer is as narrow as possible.

The superabsorbent polymer obtained from the above-mentioned procedures is an un-dissolved hydrophilic polymer, with a uniform bridging structure within the resin. In order to further improve the characteristics of the superabsorbent polymer, for example, for improving the absorption rate, for improving the gel strength, for improving the anti-blocking property and for increasing the liquid permeability, the surface of the resin is further coated with a multifunctional group cross-linking agent capable of reacting with an acid group to generate cross-linking and bridging on the surface of the superabsorbent polymer. The surface cross-linking agent and the surface cross-linking treatment are described as follows.

Specifically speaking, after screening the fixed particle size, the surface cross-linking agent coating treatment may be additionally carried out so that the surface of the superabsorbent polymer is further cross-linked. Therefore, the surface layer of the superabsorbent polymer may be processed to have a higher degree of cross-linking than its core. A superabsorbent polymer with the surface layer of a higher cross-linking degree and with the core of a lower cross-linking degree is also referred to as a superabsorbent polymer with a "core-shell structure".

The addition of the above-mentioned surface cross-linking agent varies according to various different surface cross-linking agents. For example, it can be classified as direct addition of the surface cross-linking agent, addition of the surface cross-linking agent in the form of an aqueous solution, or addition of the surface cross-linking agent after formulated in the form of hydrophilic organic solvent aqueous solution. The hydrophilic organic solvent may be selected from the group consisting of methanol, ethanol, propanol, isobutanol, acetone, methyl ether, ethyl ether . . . etc. without particular limitations as long as it forms a solution. It is preferably selected from methanol or ethanol (Please refer to U.S. Pat. No. 6,849,665). The appropriate addition of the cross-linking agent is between 0.001% and 10% by weight, based on the total solids content of the reactants, more preferably between 0.005% and 5%. When the addition of the amount of the cross-linking agent is less than 0.001% by weight, no obvious effect is exhibited, and when the addition of the amount of the cross-linking agent is 10% by weight or more, the water absorption is too low, and it results in a decrease of the resin properties.

According to one embodiment of the present invention, the above-mentioned cross-linking agent may be a cross-linking agent which can carry out a surface treatment and a reaction at the same time, for example, a polyhydric alcohol, a polyamine, a compound having two or more epoxy groups, an alkylene carbonate or the mixture thereof. In particular, the polyol may be selected from glycerol, ethylene glycol, diethylene glycol, triethylene glycol, polyethylene glycol or propylene glycol, etc., but it is not limited to these. The polyamine may be selected from ethylenediamine, di ethylenediamine or triethylenediamine, but it is not limited to these. The compounds having two or more epoxy groups may be selected from sorbitol polyglycidyl ether, polypropylene glycol polyglycidyl ether, ethylene glycol diglycidyl ether, diethylene glycol diglycidyl ether, polyethylene glycol diglycidyl ether or dipropylene glycol polyglycidyl ether, etc., but it is not limited to these. The alkylene carbonate may be selected from ethylene glycol carbonate, 4-methyl-1,3-dioxolan-2-one, 4,5-dimethyl-1,3-dioxolan-2-one, 4,4-dimethyl, 3-dioxolan-2-one, 4-ethyl-1,3-dioxolan-2-one, 1,3-dioxan-2-one or 4,6-dimethyl-1,3-dioxan-2-one or 1,3-dioxepan-2-one, but it is not limited to these. The cross-linking agent may be used alone or in combination of two or more.

Prior art references have disclosed various processes of surface cross-linking treatment, for example, by dispersing an absorbent resin and a cross-linking agent in an organic solvent for the surface cross-linking treatment (JP-A-56-131608, JP-A-57-44627, JP-A 60-A-58-22602, JP-A 58-12222), by using an inorganic powder to directly mixing a cross-linking agent and a cross-linking agent solution with an absorbent resin to carry out the surface cross-linking treatment (JP-A60-163956, JP-A-60-255814); by a vapor treatment after adding a cross-linking agent (JP-A-1-113406), by using an organic solvent, water and a polyol for the performance of the surface treatment (JP-A-1-292004, U.S. Pat. No. 6,346,569), and the use of an organic solution, water, and ether compounds (JP-A-2-153903) and the like. Although the surface cross-linking treatments which are disclosed in the current patent references can improve the absorption rate and increase the absorption against pressure, they also have an adverse consequence of excessive decline of retention to reduce the practical application of the performance. In contrast, the method of the surface cross-linking treatment demonstrated by the embodiments of the present invention does not suffer from the above-mentioned disadvantages.

After the above surface cross-linking treatment is carried out, the superabsorbent polymer after the surface cross-linking treatment is further subjected to another surface treatment with a weakly acidic aqueous solution having silicon-containing compounds to obtain a superabsorbent polymer of both the antibacterial and deodorizing abilities without reducing the water absorption properties of the absorbent resin.

According to one embodiment of the present invention, the weight ratio of the amount of the weakly acidic aqueous solution with silicon-containing compounds to the amount of the total solid content of the reactants is in the range of 0.001% to 20%, more suitably in the range of 0.005% to 10%. When the amount of the aqueous solution with the silicon-containing compounds is less than 0.001% by weight, it exhibits no obvious effect. When the amount of the aqueous solution with the silicon-containing compounds is 20% or more by weight, the water absorption ability is lowered (for example, the absorption against pressure) and the resin performance is lower.

In order to uniformly distribute the silicon-containing compounds onto the surface of the superabsorbent polymer, according to one embodiment of the present invention, a mixing device of sufficiently large mixing power may be used so that the mixing can be sufficiently uniform. The above-mentioned mixing device may be a V-type mixer, a column mixer, a high-speed blending mixer, a screw mixer, a gas mixer, a double-arm kneader, a double-arm conical mixer, a ribbon mixer, a closed system mixer, a pulverizer, a rotary mixer, or a screw extruder, but it is not limited to these.

The weakly acidic aqueous solution with the silicon-containing compounds can be obtained in either of the following two ways:

(1) Self-Prepared Weakly Acidic Aqueous Solution with Silicon-Containing Compounds An inorganic salt powder such as diatomaceous earth, soft clay, clay, talc, zeolite, kaolin, bentonite, activated clay, hydrotalcite, attapulgite or fluorite is mixed with water to obtain an aqueous solution; the inorganic salt powder can be used alone or in combination with two or more. Among them, the inorganic salt powder preferably contains alumina and silicon dioxide, for example, an aluminum-containing silicate. Among them, the alumina has the ability to adsorb odor, while the silicon dioxide has more negative charge (−200 uC/g) to render the inorganic salt powder as a whole with negative charge. Specifically speaking, the silicon-containing salt powder can cover the outer protein layer of the virus in the form of ionic bonds to damage the protein. When the virus' protein structure is destroyed, the virus fails to continue to survive and copy, so it has the effect of suppressing its growth.

It is to be noted that the weight of alumina to silica in the inorganic powder is preferably between 0.5 and 0.95, more preferably between 0.7 and 0.95, in order to achieve the ability to adsorb odor and to be bacteriostatic. For the case where the alumina content is too low, the odor absorption ability is ineffective. In addition, in the case where the alumina content is too high (i.e. the silica content is too low), the amount of charge (−200 uC/g) of the silica is much higher than the charge amount of the alumina (100 uC/g) so that the weakly acidic silicon-containing compounds have lower negative charge to result in decreased bacterial capture, and thus unable to inhibit their growth.

The average particle size of the inorganic salt powder is less than 50 μm, preferably less than 10 μm, and more preferably less than 5 μm. The weakly acidic aqueous solution with the silicon-containing compounds is needed to be formulated to be an aqueous solution with a pH between 4 and 6.5. Because the aqueous solution is weakly acidic, it is able to neutralize the ammonia compounds in the urine to further enhance the effect of reducing odor. The acidic compound used to adjust the pH may be sodium bicarbonate, sodium bisulfate, boric acid, acetic acid, tartaric acid, or citric acid. The inorganic salt powder concentration in the aqueous solution is between 0.1% and 30% by weight (based on the total solid content of the reactants), more suitably between 0.5% and 20%. When the weight percentage of the inorganic salt powder in the aqueous solution is 0.1% or lower, it cannot exhibit obvious effect. When the weight percentage of the inorganic salt powder in the aqueous solution is 30% or more, the inorganic salt powder cannot be effectively dispersed in the water.

In order to make the inorganic salt powder and the water fully mixed, the mixing device used in the mixing process must be able to produce a large mixing force, solid-liquid mixers for example: IKA MHD-200 type mixer, IKA T25 type mixer, IKA magic Lab DR mixer, FMCE-1000 mixers or Ashizawa PSI-MIX mixer.

(2) Purchase of Commercially Available Aqueous Solution with Inorganic Salt

Examples of the commercially available inorganic acid solutions of weakly acidic silicon-containing compounds include LMC-581 (manufactured by Longmao Co., Ltd.), SH-2778 (manufactured by Sunhome Co., Ltd.), MY-972 (manufactured by Ming Ye Co., Ltd.).

Please refer to FIG. 1, which is a schematic diagram of the structure of the superabsorbent polymer fabricated according to one embodiment of the present invention. A superabsorbent polymer 10 shown in FIG. 1 includes resin particles 100 with internal cross-linking structures. Each of the resin particles 100 is covered by at least a layer of silicon-containing inorganic salt-containing particles 102. Specifically, referring to the enlarged picture at the bottom of FIG. 1, at least a layer of surface cross-linked region 104 is at the surface of each of the resin particles and covered by the silicon-containing inorganic salt-containing particles 102. Preferably, the cross-linking density of the surface cross-linked region 104 is higher than the cross-linking density of the core of each resin particle 100. The detailed description of the superabsorbent polymer is disclosed in the preceding paragraphs, it is therefore omitted for the sake of clarity.

According to the above-described embodiments, the water-absorbent resin having both antibacterial and deodorizing abilities can be produced by spraying the silicon-containing compound weak acid aqueous solution onto the surface of the water-absorbent resin without reducing the water-absorbing property of the water-absorbent resin. Specifically, the weakly acidic silicon-containing compound in the water-absorbent resin can neutralize the alkaline substance in the urine to reduce the occurrence of bad odor. In addition, by the fact that the weakly acidic silicon compound has a high electric charge property, it can form a strong electrostatic attraction force to capture bacteria and inhibit its growth. In addition, by the large surface area of the weakly acidic silicon compound, it can adsorb the sulfide or amine compound in the urine to suppress the occurrence of the bad odor. On the other hand, there is no powder leakage in the production equipment, or even no suspension in the air of the plant, during the production of this absorbent resin, to harm the respiratory tracts of personnel. The methods for preparing the water-soluble unsaturated monomer described above are not particularly limited. The superabsorbent polymers produced by the method of the present invention are suitable for various types of hygienic articles, agricultural and food preservation of the water absorption agents.

The absorbent resin disclosed in the above embodiments is suitable for various types of hygienic articles, water-absorbing agents for use in agricultural and food purposes, and is particularly suitable for absorbers in diapers, in particular in Fluffless (use a lot of absorbent resin) and adult diapers.

For the absorbent resin, which is used as a diaper absorbent core, it is necessary not only to have the Centrifuge Retention Capacity (CRC), but also to have permeability under load (PUL). With respect to the absorbent resin of high absorption against pressure (AAP) and of high PUL, even when the liquid enters the liquid-absorbent core, due to high PUL, it is possible for the liquid to be easily dispersed to other water-absorbent resin which has not absorbed the liquid yet through the water-absorbent resin which has absorbed the liquid, thereby reducing the amount of rewet of the absorbent core and enhancing the dryness of the diaper. The PUL value is preferably higher than 30%, and more preferably more than 40% or more for 0.9% sodium chloride aqueous solution at a pressure of 4.9 kPa.

According to embodiments of the present invention, the absorbent core is a sheet-like structure which is made by pressing a superabsorbent polymer and a hydrophilic fiber. The absorbent core is padded with a non-permeable polymeric film, such as a PE film, and the permeable nonwoven fabric is disposed on the absorbent core to serve as a surface layer. In addition, the absorbent resin may also be fixed to Airlaid and/or a nonwoven fabric. Airlaid is pulverized wood pulp, cross-linked cellulose fibers, cotton, wool or vinyl acetate fibers, but it is not limited to these. The absorbent resin content in the absorbent core may be between 20% and 100% by weight, preferably between 40% and 100% by weight, more preferably between 50% and 100%. According to embodiments of the present invention, the basic weight (weight per unit area) of the absorbent core is between 0.01 to 0.30 g/cm$^2$ and the thickness of the absorbent core is 30 mm or less.

The absorbent resin prepared by using the above-described embodiments is used as the absorbent core in the diapers, which can be antibacterial, deodorizing and maintain the water absorption property of the water absorbent resin, thereby effectively solving the problems of the conventional diaper.

For those of ordinary skills in the art to practice the invention, the physical analysis method and the preparation method of the superabsorbent polymer and the absorbent core of the present invention will be described in further details below. It is to be noted that the following examples are illustrative only and are not intended to be limiting of the invention. Therefore, the materials, the amount and the ratio of the materials used in the examples, the processing flow, and the like can be appropriately changed without departing from the scope of the present invention. It is to be noted that the physical property analysis method described below is carried out at room temperature of 23±2° C. and the relative humidity of 45±10%, unless otherwise specified, and the absorbent resin should be thoroughly mixed before it is analyzed.

The physical property analysis methods with respect to the absorbent resin and the absorbent core are described as follows. PDAUP: Permeability Dependent Absorption under Pressure of Superabsorbent Polymer. AAP: Absorption Against Pressure. PUL: Permeability Under Load. CRC: Centrifuge Retention Capacity. RAA: Residual Monomers. Deodorizing test of the superabsorbent polymer. Antibacterial test of the superabsorbent polymer. Deodorizing bad odor test of the superabsorbent polymer. Evaluation of Rewet of the absorbent core. Deodorizing test of the absorbent core. The antibacterial test of the absorbent core.

Permeability Dependent Absorption Under Pressure (PDAUP) of Superabsorbent Polymer The test is carried out according to the test method of ERT 443.1 (5) by EDANA (European Disposables And Nonwovens Association) to test the liquid permeability of the water-absorbent resin under the pressure of 4.9 kPa. It is preferable to have 8 (g/g) or more, and more preferably 10 (g/g).

Absorption Against Pressure (AAP) of Superabsorbent Polymer

The test is carried out according to the test method of ERT 442.2(5) by EDANA (European Disposables And Nonwovens Association). Absorption is tested for 60 minutes at a pressure of 4.9 kPa with 0.9% sodium chloride aqueous solution. It is preferable to have 15 (g/g) or more, and more preferably 20-30 (g/g).

Permeability Under Load (PUL) of Superabsorbent Polymer (Unit: %)

PUL of the superabsorbent polymer is calculated by dividing PDAUP with AAP and then multiplying by 100 to change it into percent.

Centrifuge Retention Capacity (CRC) of Superabsorbent Polymer

The test is carried out according to the test method of ERT 441.3(10) by EDANA (European Disposables And Nonwovens Association).

Residual Monomers (RAA) of Superabsorbent Polymer

The test is carried out according to the test method of ERT 410.3(10) by EDANA (European Disposables And Nonwovens Association).

Deodorizing Test of Superabsorbent Polymer

Adult urine is collected and placed in a polypropylene bottle with lid (tested within two hours of urine excretion). After 2.0 g of superabsorbent polymer is add, the polypropylene bottle is covered with a lid and placed in 37° C. environment for 2 hours. Then the bottle is opened, 10 adults smell the bottle about 3 cm position atop to determine the deodorant effect. The rating level is divided into 6 grades, and the references are as follows. The final score is the average value of the total ratings and the urine taste of the same condition is set to be fifth grade without the addition of the superabsorbent polymer.

0: no odor
1: slightly feel the odor
2: feel the odor but tolerable
3: feel the odor
4: strong odor
5: bad odor Antimicrobial Test of Superabsorbent Polymer The method of AATCC100 is used to analyze the antibacterial activity of *Escherichia coli*, and it is determined to have an antibacterial activity if less *Escherichia coli* is observed in the test group than in the control group.

Deodorizing Bad Odor Test of Superabsorbent Polymer (Determination of Methyl Mercaptan Removal Ratio)

After adding 1.0 g of a superabsorbent polymer and 25 ml of an aqueous solution of 0.03% sodium methyl mercaptan in a 1-liter closed container, the mixture is allowed to stand at room temperature for 10 minutes, and then analyzed by gas detection tubes (GASTEC 4L and 4HM) to determine the residual gas concentration. The removal ratio in this test is calculated based on the reduced residual gas concentration relative to the blank test.

Evaluation of Rewet (Dryness) of Absorbent Core

A pressure of 4.8 kPa (area: 160 cm$^2$, weight: 7.8 kg) is placed on the test absorbent core so that the pressure of the weight is uniformly applied to the test absorbent core, and then the synthetic urine 180 mL (according to Jayco the synthetic urine described in U.S. Patent Publication No. 20040106745) is added in three times to the center point (30 minutes each). 30 minutes after the addition is completed, the weight on the test absorbent core is removed, 30 sheets of filter papers (8 cm×20 cm) of the total pre-measured weight (W1 (g)) are placed on the absorbent core, and the weight of 4.8 kPa is immediately placed on the test filter paper for 5 minutes to allow the filter papers to absorb the rewet liquid, then the weight of 30 sheets of filter papers (W2 (g)) is measured. The amount of the rewet liquid of the synthetic urine of the absorbent core (g) is W2−W1. The lower the amount of the rewet is, the better the urine resistance of the absorbent resin is.

Deodorization Test of Absorbent Core

A 10×10 cm$^2$ of absorbent core is taken in a glass culture dish (diameter 120 mm), after the collected adult urine is added to it, it is immediately closed with a lid (urine to be test within two hours of excretion), and the glass culture dish is placed in an environment of 37° C. for 2 hours. Then the lid is removed, 10 adults smell about 3 cm position atop to determine the deodorizing effect. The rating level is divided into 6 grades, and the references are as follows. The final score is the average value of the total ratings and the urine taste of the same condition is set to be fifth grade without the addition of the superabsorbent polymer.
0: no odor
1: slightly feel the odor
2: feel the odor but tolerable
3: feel the odor
4: strong odor
5: bad odor Antimicrobial Test of Absorbent Core A 10×10 cm$^2$ absorbent core is taken to use the method of AATCC100 to analyze the antibacterial activity of *Escherichia coli*, and it is determined to have an antibacterial activity if less *Escherichia coli* is observed in the test group than in the control group.

Hereinafter, the method of manufacturing the silicon-containing compound weak acid aqueous solution, the superabsorbent polymer, and the absorbent core will be described.

Method for Preparing Weak Acid Aqueous Solution with Silicon-Containing Compounds Preparation Example 1

20 g of kaolin (purchased from Longmao Company/LM-812, particle size=2 μm, alumina and silica weight ratio is 0.86) is slowly added to 380 g of a pH=5.0 aqueous solution of sodium bicarbonate (added in a rate of 0.25 g/min. conditions for 1.5 hours) while mixing with an IKA T25 mixer (speed 16000 rpm) and keeping the temperature of the system in the range of 5° C. to 15° C. After completion of the addition, the mixture is stirred under the same conditions for 5 minutes, to obtain the silicon-containing compound weak acid aqueous solution (1).

Method for Preparing Superabsorbent Polymer

Preparation Example 1

(1) 48% sodium hydroxide aqueous solution 437.5 g is slowly added to 540 g of acrylic acid and 583.2 g of water in a 2000 mL conical flask and the ratio of sodium hydroxide/acrylic acid is in the range of 0.85 to 0.95 for the time period of 2 hours. The temperature of the neutralizing reaction system is maintained in the range of 15° C. to 40° C. The weight percentage of the monomer in the aqueous solution is 42%, of which 70 mol % of the acrylic acid is partially neutralized to be sodium acrylate.
(2) Further, 1.1 g of N,N'-methylene-bis(acrylamide) is added to the water-soluble unsaturated monomer solution at temperature of about 20° C.
(3) 0.3 g of hydrogen peroxide, 3.6 g of sodium bisulfite and 3.6 g of ammonium persulfate starting agent are added to carry out the polymerization reaction.
(4) The gel formed after the reaction is chopped by a cutting mill then gel bodies having a particle size of 2 mm or less is screened out.
(5) They are further dried at temperature of 130° C. for 2 hours, and then screened with a screen of fixed particle size of 0.1 mm to 0.85 mm to obtain a powdery superabsorbent polymer having CRC of 40.5 g/g.
(6) 200 g of powdery superabsorbent polymer is weighted to be mixed with 5 g of a 1:1:0.5 mixed aqueous solution of ethylene glycol, 1,4-butanediol (manufactured by FOR-MOSA PLASTICS CORPORATION) and methanol, (ethylene glycol, 1,4-butanediol and methanol of 1:1:0.5 wt. %). The mixture is heated at 150° C. for 1 hour. A superabsorbent polymer is obtained after cooling off. The CRC is 32.3 g/g, the AAP is 23.7 g/g, PDAUP is 10.4 g/g, PUL=43.9%, and RAA is 352 ppm.

Preparation Example 2

(1) 48% sodium hydroxide aqueous solution 437.5 g is slowly added to 540 g of acrylic acid and 583.2 g of water in a 2000 mL conical flask and the ratio of sodium hydroxide/acrylic acid is in the range of 0.85 to 0.95 for the time period of 2 hours. The temperature of the neutralizing reaction system is maintained in the range of 15° C. to 40° C. The weight percentage of the monomer in the aqueous solution is 42%, of which 70 mol % of the acrylic acid is partially neutralized to be sodium acrylate.
(2) Further, 1.5 g of polyethylene glycol diacrylate (MW=523) is added to the water-soluble unsaturated monomer solution at temperature of about 20° C.
(3) 0.3 g of hydrogen peroxide, 3.6 g of sodium bisulfite and 3.6 g of ammonium persulfate starting agent are added to carry out the polymerization reaction.
(4) The gel formed after the reaction is chopped by a cutting mill then gel bodies having a particle size of 2 mm or less is screened out.
(5) They are further dried at temperature of 130° C. for 2 hours, and then screened with a screen of fixed particle size of 0.1 mm to 0.85 mm to obtain a powdery superabsorbent polymer having CRC of 41.3 g/g.
(6) 200 g of powdery superabsorbent polymer is weighted to be mixed with 5 g of a mixed aqueous solution of ethylene glycol, 1,4-butanediol and methanol, (the ratio of ethylene glycol, 1,4-butanediol and methanol is 1:1:0.5 wt. %). The mixture is heated at 150° C. for 1 hour. A superabsorbent polymer is obtained after cooling off. The CRC is 33.1 g/g, the AAP is 24.6 g/g, PDAUP is 12.2 g/g, PUL=49.6%, and RAA is 412 ppm.

Surface Treatment of Superabsorbent Polymer with Weakly Acidic Aqueous Solution Having Silicon-Containing Compounds Example 1

100 g of the superabsorbent polymer prepared in Preparation Example 1 is weighed to add 0.7 g of LMC-581 (Longmao Company) and mixed with a V-type mixer for 5 minutes to obtain a superabsorbent polymer. The CRC is 32.3 g/g, the AAP is 23.5 g/g, PDAUP is 10.8 g/g, PUL=46.0%, and RAA is 330 ppm.

Example 2

Example 1 is repeated with the exception that the addition amount of LMC-581 is increased to 1.5 g to prepare a superabsorbent polymer. The CRC is 32.5 g/g, the AAP is 23.3 g/g, PDAUP is 10.0 g/g, PUL=42.9%, and RAA is 361 ppm.

Example 3

Example 1 is repeated with the exception that MY-972 (Ming Ye Co., Ltd.) is used to replace LMC-518 to obtain a superabsorbent polymer. The CRC is 32.5 g/g, the AAP is 23.1 g/g, PDAUP is 10.4 g/g, PUL=45.0%, and RAA is 369 ppm.

Example 4

Example 1 is repeated with the exception that the silicon-containing compound weak acid aqueous solution (1) obtained in Preparation Example 1 is diluted (to water ratio 1:20 and pH value is 5.1) and used to replace LMC-518 to obtain a superabsorbent polymer. The CRC is 32.2 g/g, the AAP is 22.9 g/g, PDAUP is 9.5 g/g, PUL=41.5%, and RAA is 345 ppm.

Example 5

Example 4 is repeated with the exception that 2.0 g of the diluted silicon-containing compound weak acid aqueous solution (1) is used to obtain a superabsorbent polymer. The CRC is 32.1 g/g, the AAP is 22.5 g/g, PDAUP is 9.8 g/g, PUL=43.6%, and the RAA is 371 ppm.

Example 6

100 g of the superabsorbent polymer prepared in Preparation Example 2 is weighed to add 0.7 g of LMC-581 and mixed with a V-type mixer for 5 minutes to obtain a superabsorbent polymer. The CRC is 32.9 g/g, the AAP is 24.7 g/g, PDAUP is 12.4 g/g, PUL=50.2%, and RAA is 411 ppm.

Example 7

Example 4 is repeated with the exception that the superabsorbent polymer in Preparation Example 2 is used to prepare a superabsorbent polymer. The CRC is 32.7 g/g, the AAP is 23.7 g/g, the PDAUP is 11.6 g/g, PUL=48.9%, and RAA is 405 ppm.

Comparative Example 1

Example 1 is repeated, except that 1.5 g of an aqueous solution of silica (HDK D1512B, manufactured by Wacker Co., Ltd.) is used to replace LMC-518, to obtain a superabsorbent polymer. The CRC is 32.5 g/g, the AAP is 21.4 g/g, PDAUP is 6.0 g/g, PUL=28.0%, and RAA is 374 ppm.

Comparative Example 2

Example 1 is repeated with the exception that the weakly acidic aqueous solution (1) obtained in Preparation Example 1 is diluted (kaolin particle size=2 μm, to water ratio 1:20 and pH value is 7.1) to replace the silica aqueous solution to obtain a superabsorbent polymer. The CRC is 32.5 g/g, the AAP is 22.7 g/g, PDAUP is 6.5 g/g, PUL=22.7%, and RAA is 381 ppm.

Comparative Example 3

Example 4 is repeated with the exception that attapulgite (Longmao Co., Ltd., average particle size=5 μm, and alumina to silicon oxide ratio 0.12) is used to replace the weakly acidic aqueous solution (1) to obtain a superabsorbent polymer. The CRC is 32.3 g/g, the AAP is 21.1 g/g, PDAUP is 5.2 g/g, PUL=24.6%, and RAA is 435 ppm.

Comparative Example 4

The superabsorbent polymer fabricated in Preparation Example 1 is Comparative Example 4.

Comparative Example 5

The superabsorbent polymer fabricated in Preparation Example 2 is Comparative Example 5.

TABLE 1

| | Deodorization Test | Antimicrobial Test | Deodorizing Bad Odor Test |
|---|---|---|---|
| Example 1 | 3 | positive | 71% |
| Example 2 | 1 | positive | 87% |
| Example 3 | 3 | positive | 79% |
| Example 4 | 3 | positive | 81% |
| Example 5 | 2 | positive | 85% |
| Example 6 | 3 | positive | 74% |
| Example 7 | 2 | positive | 83% |
| Comparative Example 1 | 5 | negative | 37% |
| Comparative Example 2 | 4 | positive | 43% |
| Comparative Example 3 | 5 | positive | 33% |
| Comparative Example 4 | 5 | negative | 3% |
| Comparative Example 5 | 5 | negative | 5% |

Preparation Method of Absorbent Core

Preparation Example 1

The absorbent resin obtained in Preparation Example 1 is prepared by mixing 10.0 g of the absorbent resin and 10.0 g of the pulverized wood pulp using an absorber molding machine. The metal mesh is of 400 mesh (38 μm) and the absorbent core has surface area 160 cm² (8 cm×20 cm). The formed absorbent core is placed on top of a PE film and then a nonwoven fabric is placed, followed by pressing the absorbent core with a pressure of 18.39 kPa (weight 30 kg on 160 cm²) for 5 minutes and a white glue is used to glue the periphery to obtain the absorbent core (1). The basis weight of the absorbent core (1) is 0.07 g/cm² and the thickness is 17 mm.

Preparation Example 2

The absorbent resin in Example 2 is taken to obtain the absorbent core (2) by the method which is similar to that described in Preparation Example 1. The basis weight of the absorbent core (2) is 0.07 g/cm² and the thickness is 16 mm.

Preparation Example 3

The absorbent resin in Example 3 is taken to obtain the absorbent core (3) by the method which is similar to that described in Preparation Example 1. The basis weight of the absorbent core (3) is 0.07 g/cm² and the thickness is 16 mm.

Preparation Example 4

The absorbent resin in Example 4 is taken to obtain the absorbent core (4) by the method which is similar to that described in Preparation Example 1. The basis weight of the absorbent core (4) is 0.08 g/cm² and the thickness is 15 mm.

Preparation Example 5

The absorbent resin in Example 5 is taken to obtain the absorbent core (5) by the method which is similar to that described in Preparation Example 1. The basis weight of the absorbent core (5) is 0.07 g/cm² and the thickness is 15 mm.

Preparation Example 6

The absorbent resin in Example 7 is taken to obtain the absorbent core (6) by the method which is similar to that described in Preparation Example 1. The basis weight of the absorbent core (5) is 0.08 g/cm2 and the thickness is 14 mm.

Comparative Example 1

Preparation Example 1 is repeated except that the superabsorbent polymer prepared in Comparative Example 1 is used to obtain an absorbent core (7). The basis weight of the absorbent core (7) is 0.07 g/cm² and the thickness is 16 mm.

Comparative Example 2

Preparation Example 1 is repeated except that the superabsorbent polymer prepared in Comparative Example 2 is adopted to obtain an absorbent core (8). The basis weight of the absorbent core (8) is 0.08 g/cm² and the thickness is 15 mm.

Comparative Example 3

Preparation Example 1 is repeated except that the superabsorbent polymer prepared in Comparative Example 3 is adopted to obtain an absorbent core (9). The basis weight of the absorbent core (9) is 0.07 g/cm² and the thickness is 16 mm.

Table 2 is the performance evaluation of the results of the deodorizing test and of the antibacterial test of the absorbent cores.

TABLE 2

|  | Deodorization Test | Antimicrobial Test | Rewet of Synthetic Urine |
|---|---|---|---|
| Preparation Example 1 | 3 | positive | 2.1 g |
| Preparation Example 2 | 2 | positive | 2.8 g |
| Preparation Example 3 | 3 | positive | 2.5 g |
| Preparation Example 4 | 2 | positive | 3.2 g |
| Preparation Example 5 | 3 | positive | 2.7 g |
| Preparation Example 6 | 3 | positive | 2.9 g |
| Comparative Example 1 | 5 | negative | 7.3 g |
| Comparative Example 2 | 4 | negative | 8.5 g |
| Comparative Example 3 | 5 | negative | 8.9 g |

It is to be noted that, by the comparison of Table 1 with Table 2, since only the superabsorbent polymer in the absorbent cores has the deodorant and antibacterial properties, while the wood pulp and the nonwoven fabric do not have such properties, so the performance evaluation of the results of the deodorizing test and of the antibacterial test of the absorbent cores as shown in Table 2 is slightly lower than that of the absorbent resin as shown in Table 1.

Figure 1:
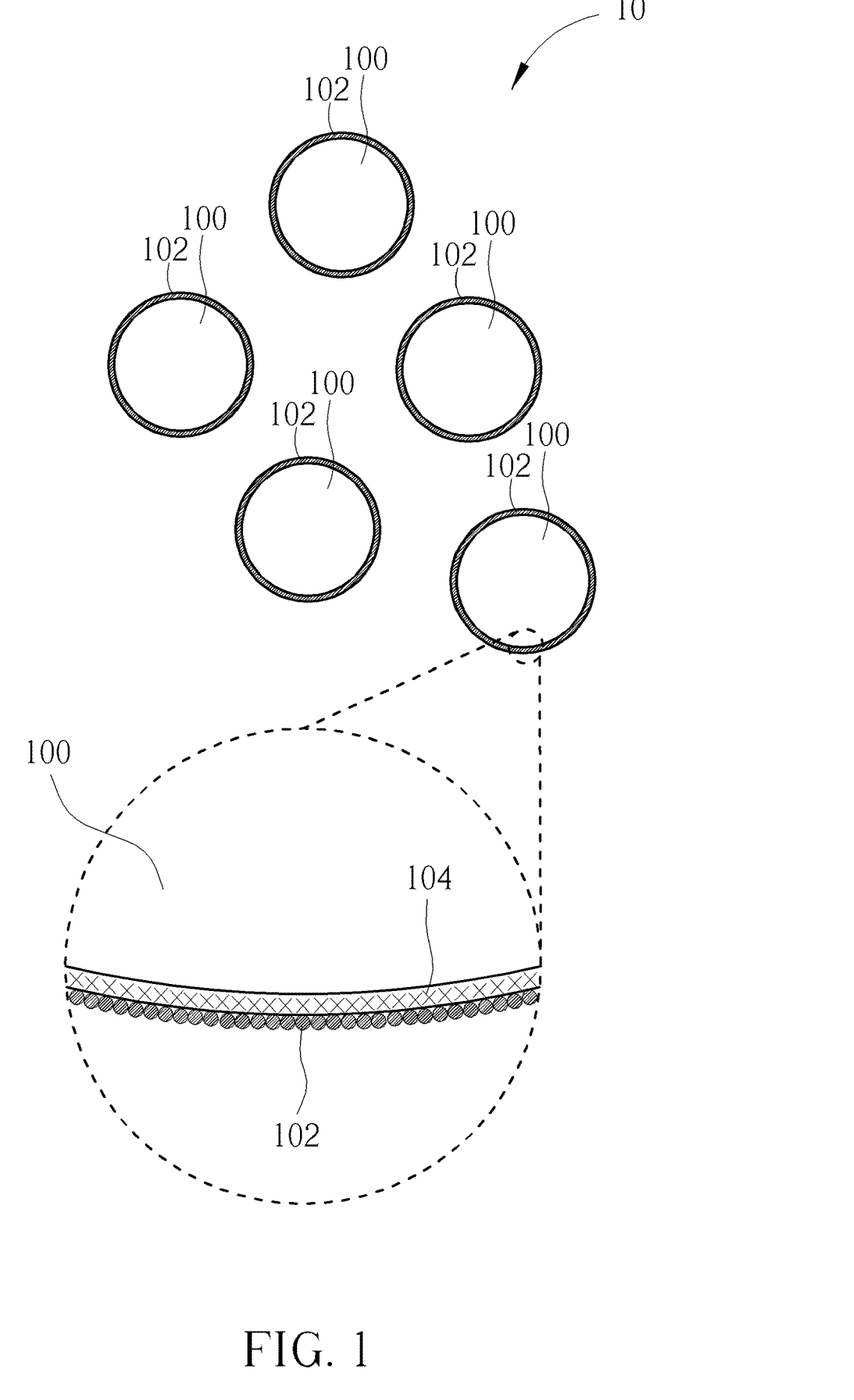
FIG. 1 is schematic diagram of the structure of superabsorbent polymer according to one embodiment of the present invention.
Figure 2:
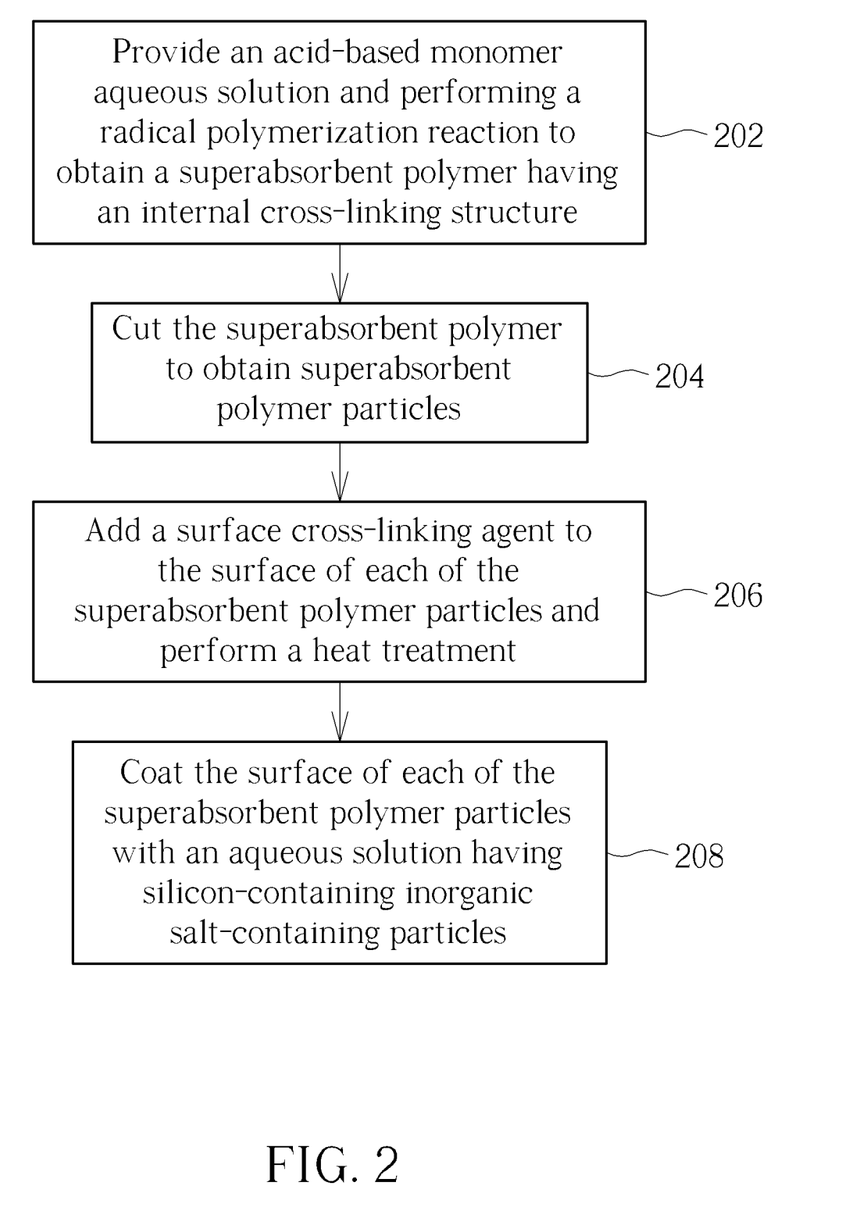
FIG. 2 is flow chart of a method for producing a superabsorbent polymer according to one embodiment of the present invention.

A method for producing a superabsorbent polymer is also provided according to one embodiment of the present invention. The method referring to FIG. 2, includes at least the following steps of: (step 202) providing an acid-based monomer aqueous solution and performing a radical polymerization reaction to obtain a superabsorbent polymer having an internal crosslinking structure; (step 204) cutting the superabsorbent polymer to obtain superabsorbent polymer particles; (step 206) adding a surface cross-linking agent to the surface of each of the superabsorbent polymer particles and perform a heat treatment so as to constitute a surface cross-linked region at the surface of each resin particle; (step 208) coating the surface of each of the superabsorbent polymer particles with an aqueous solution having silicon-containing inorganic salt-containing particles.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for producing a superabsorbent polymer, comprising:
providing an acid-based monomer aqueous solution and performing a radical polymerization reaction to obtain a superabsorbent polymer having an internal crosslinking structure;
cutting said superabsorbent polymer to obtain a plurality of superabsorbent polymer particles;
adding a surface cross-linking agent to a surface of each of said superabsorbent polymer particles and performing a heat treatment so as to constitute a surface cross-linked region at the surface of each said resin particle; and
coating said surface of each of said superabsorbent polymer particles with an aqueous solution having silicon-containing inorganic salt-containing particles, wherein a pH value of said aqueous solution having said silicon-containing inorganic salt-containing particles is between 4 and 6.5.

2. The method for producing a superabsorbent polymer of claim 1, wherein a weight percentage of said aqueous solution having said silicon-containing inorganic salt-containing particles to said superabsorbent polymer particles is between 0.5% to 20%.

3. The method for producing a superabsorbent polymer of claim 1, wherein a weight ratio of alumina to silicon oxide in said silicon-containing inorganic salt-containing particles is between 0.7 and 0.95.

4. The method for producing a superabsorbent polymer of claim 1, wherein each of said silicon-containing inorganic salt-containing particles has a particle size between 1 and 10 µm.

5. The method for producing a superabsorbent polymer of claim 1, wherein each of said silicon-containing inorganic salt-containing particles is composed of kaolinite.

* * * * *